US008838738B2

(12) United States Patent
Lee et al.

(10) Patent No.: US 8,838,738 B2
(45) Date of Patent: Sep. 16, 2014

(54) SYSTEM AND METHOD FOR PROCESSING MEDICAL INFORMATION THROUGH MEDICAL TERMINAL

(75) Inventors: Han-ku Lee, Seoul (KR); Hyo-Gun Yoon, Daejeon (KR); Myoung-Jin Kim, Dongducheon (KR)

(73) Assignee: Konkuk University Industrial Cooperation Corp., Seoul (KR)

( * ) Notice: Subject to any disclaimer, the term of this patent is extended or adjusted under 35 U.S.C. 154(b) by 381 days.

(21) Appl. No.: 13/329,424

(22) Filed: Dec. 19, 2011

(65) Prior Publication Data

US 2013/0132511 A1 May 23, 2013

(30) Foreign Application Priority Data

Nov. 23, 2011 (KR) ........................ 10-2011-0123104

(51) Int. Cl.
*G06F 15/16* (2006.01)
*H04W 4/00* (2009.01)
*G06F 19/00* (2011.01)
*H04L 29/06* (2006.01)

(52) U.S. Cl.
CPC ............ *H04W 4/003* (2013.01); *G06F 19/328* (2013.01); *G06F 19/327* (2013.01); *H04L 63/107* (2013.01)
USPC ............ 709/217; 709/218; 709/219; 709/224

(58) Field of Classification Search
CPC ............ H04L 12/2458; H04L 12/2639; H04L 29/06034; H04L 29/08846; H04L 67/025
USPC ................................ 709/217, 218, 219, 224
See application file for complete search history.

(56) References Cited

U.S. PATENT DOCUMENTS

| | | | |
|---|---|---|---|
| 7,644,171 B2* | 1/2010 | Sturniolo et al. ............. | 709/230 |
| 8,364,819 B2* | 1/2013 | Ferris et al. .................... | 709/226 |
| 2006/0123079 A1* | 6/2006 | Sturniolo et al. ............. | 709/203 |
| 2007/0265000 A1* | 11/2007 | Hanson et al. ............. | 455/432.1 |
| 2010/0332617 A1* | 12/2010 | Goodwin et al. ............. | 709/219 |
| 2011/0191122 A1* | 8/2011 | Kharraz Tavakol et al. ...... | 705/3 |
| 2011/0213687 A1* | 9/2011 | Ferris et al. ..................... | 705/34 |
| 2012/0096524 A1* | 4/2012 | Kovalan ............. | 726/5 |
| 2012/0158947 A1* | 6/2012 | Hassan et al. ................. | 709/224 |
| 2012/0304262 A1* | 11/2012 | Cucco et al. ...................... | 726/6 |
| 2013/0103844 A1* | 4/2013 | Bulut et al. ................... | 709/228 |
| 2013/0325927 A1* | 12/2013 | Corbett et al. ................ | 709/203 |

* cited by examiner

*Primary Examiner* — Tammy Nguyen
*Assistant Examiner* — Jonathan Bui
(74) *Attorney, Agent, or Firm* — Lexyoume IP Meister, PLLC

(57) ABSTRACT

Provided is a system and method for processing medical information through a medical terminal. The system includes a mobile cloud system unit and a service browser unit. The service browser unit is configured as an application in a user terminal to allow a user to use a medical information processing service, and induces access to the mobile cloud system unit taking charge of medication information processing.

8 Claims, 5 Drawing Sheets

SYSTEM AND METHOD FOR PROCESSING MEDICAL INFORMATION THROUGH MEDICAL TERMINAL

CROSS-REFERENCE TO RELATED APPLICATIONS

This U.S. non-provisional patent application claims priority under 35 U.S.C. §119 of Korean Patent Application No. 10-2011-0123104, filed on Nov. 23, 2011, the entire contents of which are hereby incorporated by reference.

BACKGROUND

The present disclosure herein relates to a system and method for processing medical information through a medical terminal, and more particularly, to a system and method for processing medical information through a medical terminal that provides optimal medical information service to a user by managing an integrated medical information processing system independently operated using a mobile cloud system.

Domestic medical information processing technology includes Picture Archiving Communication System (PACS), Order Communication System (OCS), and Electronic Medical Record (EMR), which comply with Health Level 7 (HL7). Medical information processing is independently managed by individual hospitals. Particularly, EMR has been developed into the Electronic Health Record (EHR) concept that is a lifetime electronic health record of individual patients.

However, EHR independently operated need to be integrated according to standardization for high quality medical service of individuals. For this, integrated system technology is needed, and, for example, a cloud computing model and a mobile browser are being applied.

Also, in order to concretely solve accessibility and medical information integrated service, distributed approach, user authentication portable medical information for managing medical information, information restriction necessary for service, access control technology and privacy protection, and security technology against intrusion from the outside are being used.

Medical information technology includes medical terms, reference models, forms of medical records, messaging methods, and technologies and interfaces such as medical information security as technical standards based on HL7.

Also, XML and ebXML based on message for data transmission between these systems are being discussed.

Accordingly, integration into a large capacity system and integrated management models are needed for increase of adaptability and mutual operability, intellectual property, harmony with standardization, cooperation between standardization organizations.

Also, as the distribution of smart user devices exponentially increases, usage environment of medical information service is changing. Accordingly, service usage environment building is needed to ensure the accessibility to the medical information service.

Cloud computing is a next generation computing technology in which Software as a Service (SaaS) for web 2.0 service and utility computing are complexly combined.

The service structure of cloud computing may include a server for using IT environment, storage, Infrastructure as a Service (IaaS) for serving SW infra, Platform as a Service for providing a basis for development of software, Software as a Service (SaaS) in which a computing provider supplies and uses software such as ERP and CRM through Internet.

Mobile browser technology is software-manufacturing technology with an app structure used to independently provide developed services to a user in a smart environment. Mobile browser is being developed using NDK. Since the mobile browser is developed with a hybrid web structure, it includes a function of controlling devices.

Also, mobile browser is developed using Node.js for executing JavaScript connected with a web server. Node.js, which is a non-blocking I/O API of SingleThreadModel, is a framework having the advantages of JavaScript. For an optimized structure in a mobile device, it can be divided into an application program server, a cache server, and a DB server.

Accordingly, in a structure than can process in parallel access to a server system in a mobile device, service request and work have a synergy effect including background processing, low level networking, file system access, and binary data processing.

As a related art, Korea Patent Publication No. 1020040013491 discloses "method for servicing medical treatment based on-line". The method includes providing a web page in which medical treatment reservation information including mobile communication subscriber number and medical institution selection information can be input to a user logging on a medical service server through Internet, processing the medical treatment reservation information input through the web page into a medical treatment reservation application message and then transmitting the medical treatment reservation application message to the corresponding medical institution, creating an authentication code pre-agreed on by the medical institution based on the medical treatment reservation information when a medical treatment reservation approval message is received from the medical institution, and transmitting the created authentication code to the mobile communication subscriber number such that a medical treatment reception procedure can be performed by extracting the medical treatment reservation information from the authentication code from the medical institution to a mobile communication terminal. Here, the authentication code is provided to a user, and then the medical institution uses the user authentication code to perform the reception procedure. Accordingly, the off-line administration procedure may be simplified, thereby providing convenience to a user and an institution.

As another related art, Korea Patent Publication No. 1020010074303 discloses "system for managing medical insurance using information communication network and method therefore". The system uses a smartmedia card storing personal information of medical insurance beneficiaries, information related to medical insurance, and on-line access information as a medical insurance card. Medical treatment history of a corresponding medical insurance beneficiary can be inquired by on-line information access through the smartmedia medical insurance card, and the medical insurance premiums and medical treatment fee (patient charge) generated from various kinds of medical treatments are immediately charged on-line, and the payment is authenticated.

SUMMARY

The present disclosure provides a method for sharing medical information processing service in which medical information processing systems and health care services independently operated are integrated for each person and interactive medical information of real-time structure, and a method for processing integrated medical information, which are medical information processing integrated service technology providing medical information divided by user using a smart phone terminal.

Embodiments of the inventive concept provide systems for processing medical information through a medical terminal, including: a mobile cloud system unit; and a service browser unit configured as an application in a user terminal to allow a user to use a medical information processing service, and inducing access to the mobile cloud system unit taking charge of medication information processing, wherein the service browser unit includes: a user interface module providing a service application of an icon type to the user through access identification and location information of the user using a mobile browser; an event module generating event information for extracting a module for configuring a service necessary in each region of a mobile cloud server configuring the medical information processing service; a session module managing a network environment of the user and maintaining a connection situation according to a change of the network environment; a conversion module encoding and converting the information into a compression code according to a predetermined protocol; a security module encoding the user information configured by the conversion module to securely configure virtualization of the mobile cloud server together with user access information; a network module delivering the user information to the mobile cloud system unit and monitoring a network state; and a service handler configuring a user interface with the information received from the mobile cloud system unit, sensing an interface touch operation, and monitoring a service operation, and the user connected to the medical information processing service configures a situation information showing a user situation in a smart phone to transmit to the mobile cloud system unit in real-time, and submits the user situation information generated in the interface module and the event information generated in the event module to the mobile cloud system unit.

In some embodiments, the systems may further include a medical information processing software module including: an adjustment module providing medical information divided by service user and a service corresponding thereto; a scheduler module adjusting a schedule according to the service; a distributed data module dividing data by type and clustering the data; and a platform connection module providing a connection function of platforms managing resources, and usable in a smart phone and processing medical information in real-time.

In other embodiments, the service browser unit may include an interface function of accessing from a smart phone to a cloud system and a function of outputting and managing data generated by the user touch operation and service software processing an event generated by the touch operation and expressed as an icon usable by user.

In still other embodiments, the scheduler module may include: a medical information scheduling module processing an event of a user received from a mobile device and analyzing service information; a service resource scheduling module managing software resources, hardware resources, and authority to use service application for checking a service state value from the user information and outputting the service information; and a service distribution scheduling module managing and distributing medical information and service scheduling, and authority transfer for service resources of the service resource scheduling module.

In even other embodiments, the distributed data module may have a function of classifying data used by users, and clustering the data to store location, characteristics, and grade in a metadata database and retrieving the data by characteristics.

In yet other embodiments, the platform connection module may provide a function of connecting between platforms for managing a cloud system for medical information processing and information resources and may allow a smart phone terminal including a function of virtualizing resources necessary for service processing to access the cloud system.

In further embodiments, the medical information scheduling module may provide a function of analyzing medical information necessary for service and securing a relationship therebetween to support a decision-making necessary for medical service, in a mobile cloud system receiving an operation that a user receiving medical information adjusted according to a user grade and service application performs in a smart phone as an event.

In still further embodiments, the service resource scheduling module may provide a function of checking the state value according to an operation of a service event generated from a smart phone terminal by a user, securing an authority to use and access a service application for transmitting information necessary for a service to a browser, and collecting software resources and hardware resource necessary for the service to manage all resources used for the service.

In even further embodiments, the service distribution scheduling module may provide a function of assigning a storage space and service resources to the service information provided to a user according to utilization degree thereof and monitoring and managing the service information, and outputting details of resources and packet distribution for delivering the information provided to a user on a screen.

In yet further embodiments, the systems may further include an adjustment module for providing medical information divided by service user and a service corresponding thereto. Here, the adjustment module may include: a user access adjustment module managing adjustment of user grades for processing and information access limitation; and an application adjustment module adjusting and providing a service application provided according to the grade of a user connected to a mobile cloud system supporting medical information integration processing.

In other embodiments of the inventive concept, methods for processing medical information through a medical terminal, including: configuring a service browser unit as an application in a user terminal to allow a user to use a medical information processing service and inducing access to a mobile cloud system unit taking charge of medication information processing, providing, by a user interface module, a service application of an icon type to the user through access identification and location information of the user using a mobile browser; generating, by an event module, event information for extracting a module for configuring a service necessary in each region of a mobile cloud server configuring the medical information processing service; managing, by a session module, a network environment of the user and maintaining a connection situation according to a change of the network environment; encoding and converting, by a conversion module, the information into a compression code according to a predetermined protocol; encoding, by a security module, the user information configured by the conversion module to securely configure virtualization of the mobile cloud server together with user access information; delivering, by a network module, the user information to the mobile cloud system unit and monitoring a network state; and configuring, by a service handler, a user interface with the information received from the mobile cloud system unit, sensing an interface touch operation, and monitoring a service operation.

BRIEF DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION OF THE EMBODIMENTS

Figure 1:
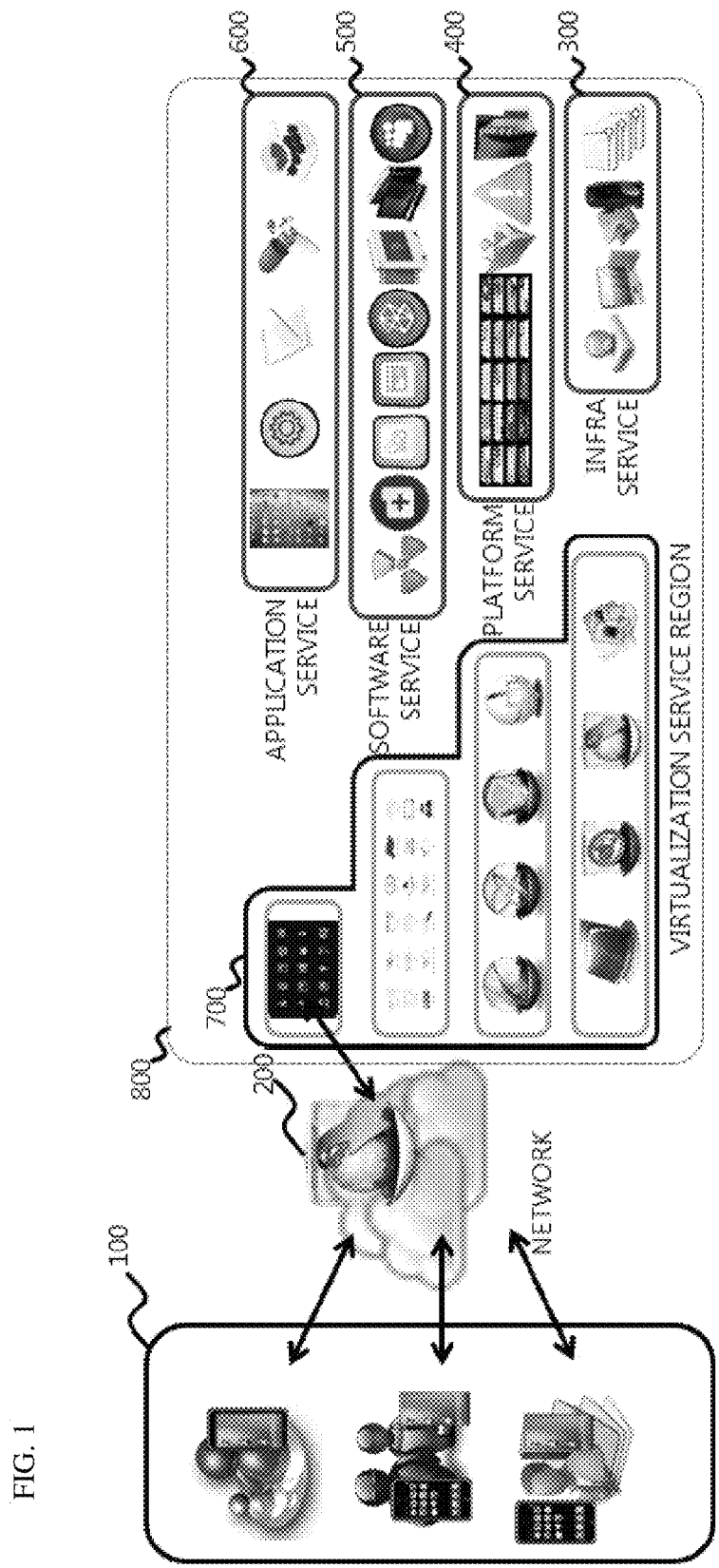
FIG. 1 is a block diagram illustrating a system for building mobile cloud computing, which divides integrated medical information by individual in a smart phone and provide service.

Exemplary embodiments of the inventive concept will be described below in more detail with reference to the accompanying drawings. The inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art.

Hereinafter, exemplary embodiments of the inventive concept will be described in detail with reference to the accompanying drawings.

The inventive concept will now be described more fully with reference to the accompanying drawings, in which exemplary embodiments of the invention are shown. It is also noted that like reference numerals denote like elements in appreciating the drawings. Moreover, detailed descriptions related to well-known functions or configurations will be ruled out in order not to unnecessarily obscure subject matters of the inventive concept.

Figure 2:
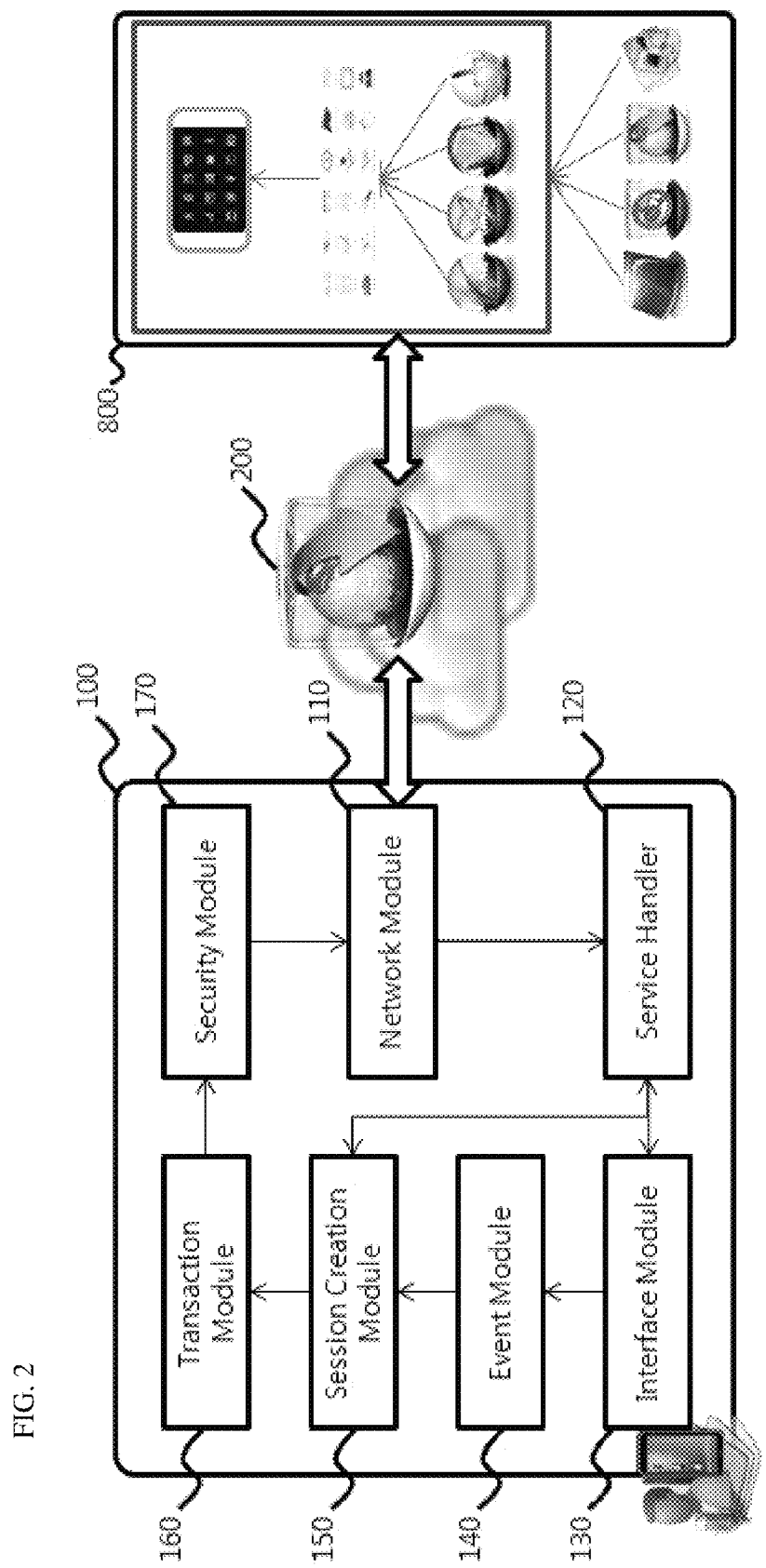
FIG. 2 is a block diagram illustrating an interface structure for mutually processing medical information processing service by individual in a smart phone terminal of FIG. 1.

As shown in FIGS. 1 and 2, in a medical information processing system using a medical terminal, a mobile medical information processing cloud system in which information processing services are integrated may be accessed using information processing tools such as smart phone terminals and personal computers. A user may be endowed with access authority and use medical information service in real-time according to his/her demand.

The medical information processing system using the medical terminal may include a mobile cloud system 800 and a service browser 100 that is included in a terminal of a user in a form of application to allow the user to use a medical information processing service and induces access to the mobile cloud system 800 taking charge of medical information processing.

Specifically, the service browser unit 100 may include a user interface module 130 providing a service application of an icon type to the user through access identification and location information of the user using a mobile browser, an event module 140 generating event information for extracting a module for configuring a service necessary in each region of a mobile cloud server configuring the medical information processing service, a session module 150 managing a network environment of the user and maintaining a connection situation according to a change of the network environment, a conversion module 160 encoding and converting the information into a compression code according to a predetermined protocol, a security module 170 encoding the user information configured by the conversion module to securely configure virtualization of the mobile cloud server together with user access information, a network module 110 delivering the user information to the mobile cloud system unit 800 and monitoring a network state, and a service handler 120 configuring a user interface with the information received from the mobile cloud system unit 800, sensing an interface touch operation, and monitoring a service operation.

Accordingly, a user connected to the medical information processing service may configure a situation information showing a user situation in a smart phone to transmit to the mobile cloud system unit 800 in real-time, and may submit the user situation information generated in the interface module 130 and the event information generated in the event module to the mobile cloud system unit 800.

The mobile cloud system 800 including the cloud system for processing medical information may include a platform connection unit 400, a medical information processing management software unit 500, an application unit 600, and a mobile service virtualization unit 700. The platform connection unit 400 may constitute a service platform. The medical information processing management software unit 500 may include open-type software and constitute a basis of an application for each user. The application unit 600 may include applications provided according to user's situations. The mobile service virtualization unit 700 may include services provided to each user.

More specifically, the mobile cloud system 800 providing services to a user may include a typical structure that provides a cloud service.

Among service regions, an infra service region may include typical hardware apparatuses.

A platform service region may constitute a service using a platform with an open-type structure according to standardization.

Also, a software service region may include open-type software, and service software necessary of medical information processing service may include open-type API, and may organize a service application.

An application region may include services necessary for medical information processing service. The application region may basically include personal medical information management service, reservation service, personal medical treatment recording service, self-diagnosis service, and other services for checking a user's medical service, and may include addition services. Also, the application region may include patient management service, medical insurance management service, and institution management service for users of medical institutions.

Figure 3:
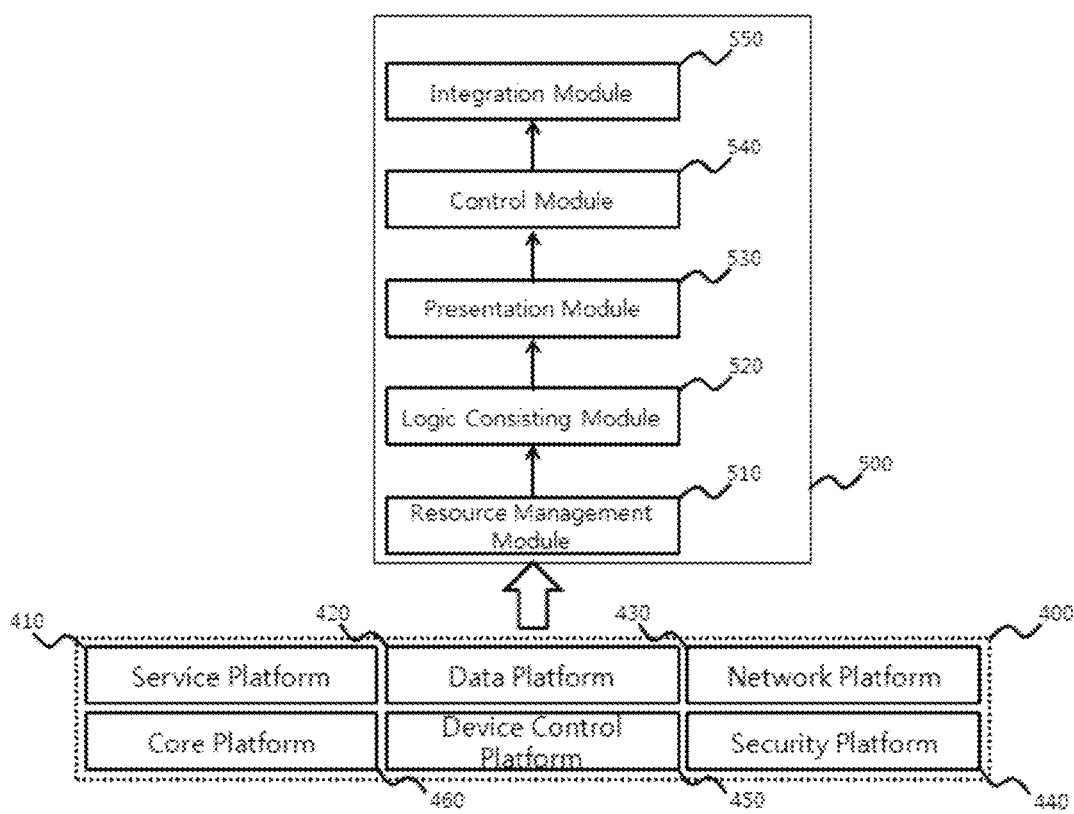
FIG. 3 is a block diagram illustrating a platform of a mobile cloud server for medical information processing shown in FIG. 1.

Finally, the application region may include medical institution management service and medical insurance management service for government managers, and may include manuals for mobile clouds service managers. Each service may be provided in a form of icon on a user interface, and may have a personalized interface structure that varies in its service interface configuration according to user's apparatuses for using service As shown in FIG. 3, the platform connection unit 400 including platforms for the medical information processing service may include platforms for increasing utilization of infra resources and service configuration.

First, a service platform 410 may have a function of constituting software service for a user and connecting infra resources in accordance with the user environment.

The service platform 410 may determine a service use tool using access information of a user, and may include service resources, platform operations, and software service in accordance with user's situation.

A data platform 420 may have a function of connecting database information and a storage space provided to a user.

Since information provided to a user varies with user identification information, database may be configured in accordance with users, and accessibility to service information may be ensured.

A network platform 430 may check the access state of a user and maintain the session. Also, the network platform 430 may check the state of a network such as internet and intranet of a mobile cloud service and manage the transmission speed of the network to maintain service.

A security platform 440 may set service securities that are divided by user and service because the access types of users are different from each other.

Basically, the security platform 440 may check the role of firewall and data protection through encoding and data compression. A device controlling platform 450 may have a function of managing physical resources of the servers used for service and distributing resources necessary for virtualization. Each physical device may have a distributed structure that checks the access state of a user and distributes service resources. Accordingly, accessibility of a user may be ensured, and provide the usage efficiency of resources for service.

A core platform 460 may manage the cores of software executed for each service in the mobile cloud service, and may manage virtualization cores of resource necessary for service virtualization and open-type API distribution, which are operated according to each core.

The medical information processing management software unit 500 of the mobile cloud server for medical information processing service may directly configure service provided to a user.

Software necessary for medical information processing may have a function of selecting software according to the service configuration of a user in the platform connection unit 400.

A resource management module 510 may be mounted with a data division module that divides data using user information, and may select user situation information and service resource necessary for service.

The resource management module 510 may include software in which selected resources are provided by type of users, and may permit access to service icons and data.

Therefore, a user may freely access his/her own data by software that the user is using.

A logic configuration module 520 may secure connectivity to platform resources, physical resources, and software resources selected by the resource management module, and may configure a service logic in accordance with the state of a user and the service use conditions.

An expression module 530 may define the data expression structure and the service resources that are expressed with icons according to the service logic of a user. The data expression structure may be expressed with XML schema in compliance with HL7 standards. Also, a data link may be expressed for secure retrieval and expression of data.

A control module 540 may include a management module that performs the control of service software and the control and management of service resources for each institution.

The control module 540 may configure software provided to managers for service software of a user, data and resource management of medical institutions, and data management of government agencies.

Software services passing through this process may be configured with open-type software and API, and may ensure software connectivity by configuring classes ensuring connectivity of each software by module.

The software service extracted for medical information processing may be integrated into one by an integration module 550 in accordance with an application to be provided to a user.

Figure 4:
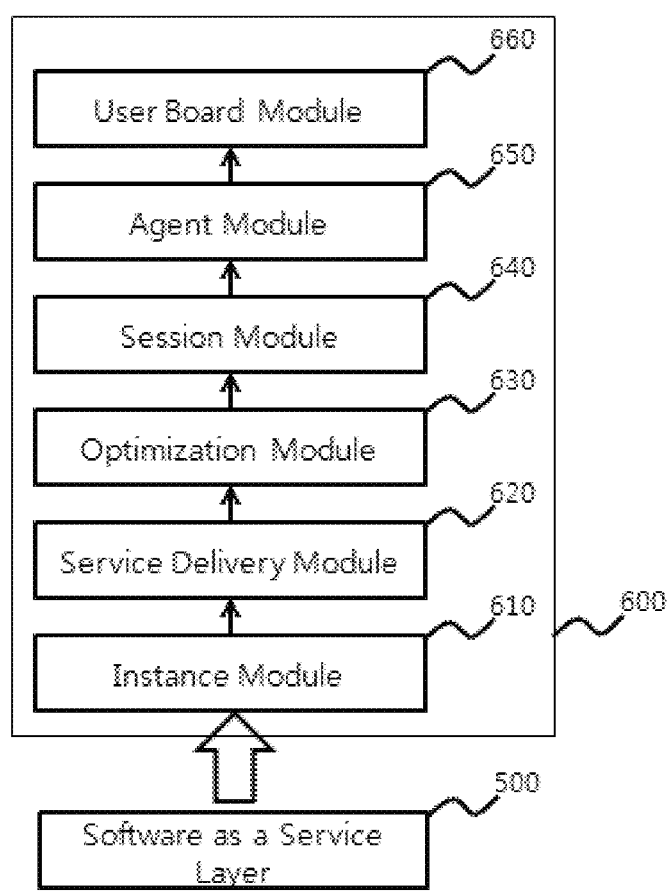
FIG. 4 is a block diagram illustrating software of a mobile cloud server for medical information processing shown in FIG. 1.

As shown in FIG. 4, the application unit 600 of the mobile cloud service for medical information processing service may configure service that is directly provided to a user using platforms and software.

An instance module 610 may call instances of platforms and software configured in the previous stage to provide service data and software in accordance with the user situations. A service delivery module 620 having a function of combining the called instances may configure service in accordance with service use of a user. The instance module 610 may take charge of icon connection for each service resource, and may extract data necessary for user service.

An optimization module 630 may undergo an optimization process using a service optimization algorithm in consideration of user service situations configured in the service delivery module 620 in accordance with use apparatuses.

Accordingly, service access time and data processing time of the user apparatus may be saved, and the best service state may be maintained.

A session module 640 may check an access signal of a user and register a session of a user in the mobile cloud server. The session module 640 may manage the interruption state of connection to check the state when the connection is forcibly interrupted and preserve service and data. An agent module 650 may have a function of managing the service state of a user and continuously monitoring and providing necessary resources to a user in the mobile cloud service. Therefore, automated service configuration may be supported in consideration of the service situation of a user.

Finally, a user board module 660 configuring service with user connection may combine a service browser of a user and an application icon in accordance with the service standard of a user. Also, the user board module 660 may check the service use state of a user, and may log data on service resources used according to service situations.

Figure 5:
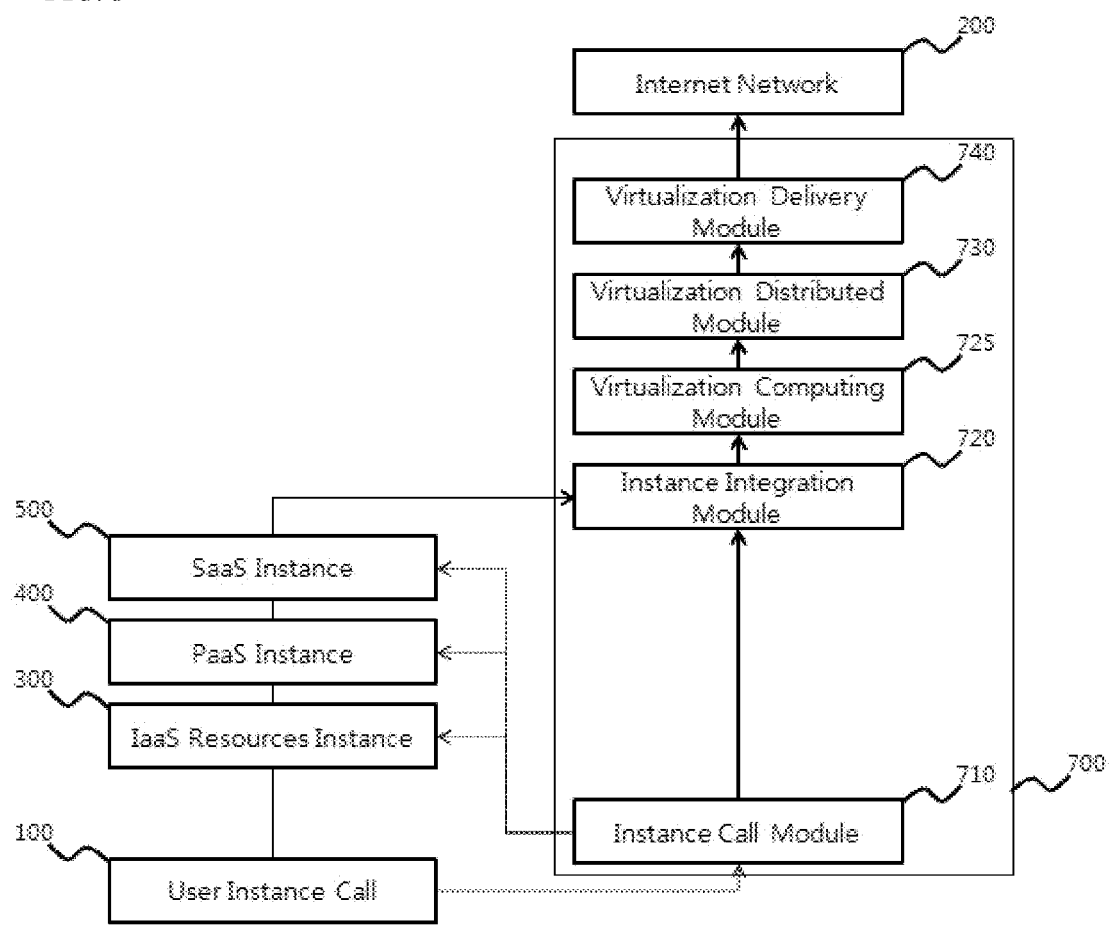
FIG. 5 is a block diagram illustrating an application service of a mobile cloud server for medical information processing shown in FIG. 1.

As shown in FIG. 5, the mobile service virtualization unit 700 of the mobile cloud server for medical information processing service may be used to securely provide medical information processing service to a user, and may have a function of increasing service security.

An instance call module 710 may call infra resources and platforms of the mobile cloud service and instances of applications configured in software to reconfigure in accordance with the user situations. This function may include a scheduler module for scheduling service in accordance with information analyzed using use information, situation information, and the service instance call information 100 of a user An instance integration module 720 may adjust virtualization by integrating the instances that are called. Since this module includes a module configuring a service menu of a user, icons constituting the mobile service browser that is a user interface may be called.

A virtualization calculation module 725 may calculate resources for providing virtualization images in accordance with the user situations using the service resources that the mobile cloud server has. Therefore, service in accordance with the apparatus of a user and its function may be provided, and a backup function may be secured.

A virtualization distribution module 730 may distribute virtualization images of medical information processing service that is basically configured according to the number of user accesses. The virtualization distribution module 730 may have a function of supplying power to an additional server according to the idle state of the mobile cloud server or collecting peripheral apparatuses to utilize for service.

Thus, the virtualization distribution module 730 may secure stability of user service, and may provide the maximum of effect with the minimum of resources.

A virtualization delivery module 740 may include virtualization images that are directly provided to a service browser installed in a smart device of a user.

The virtualization images may be derived from virtualization service that is configured with service resources necessary for medical information process and service situations of a user analyzed in the previous stages.

Accordingly, a user may be provided with specialized services configured by user who uses services of the medical information processing system through a medical terminal according to an embodiment of the inventive concept.

Hereinafter, a method for processing medical information through a medical terminal according to an embodiment of the inventive concept will be described in detail.

First, an application may be configured in a user terminal to allow a user to use medical information processing service through a service browser unit, and access to the mobile cloud system unit taking charge of medical information processing may be induced.

A service application of an icon form may be provided to a user through location information and access identification of a user using a mobile browser through a user interface module.

Even information may be generated for module extraction to configure necessary services in each region of the mobile cloud server that configures medical information processing service through an event module.

Also, network environment of a user may be managed through a session module, and connection situation may be maintained according to the change of the network environment.

The above information may be encoded or converted into compression codes according to designated protocols through a conversion module.

In order to securely configure the virtualization of the mobile cloud service together with access information of a user through a security module, the user information configured by the conversion module may be encoded.

The user information may be delivered to the mobile cloud system unit through a network module. The network state may be monitored, and the user interface may be configured using information received from the mobile cloud system unit through a service handler. The interface touch operation of a user may be detected, and a service operation may be monitored to provide a limited access to a corresponding application on the browser of a smart phone terminal. Accordingly, optimized medical information service can be provided to a user.

Also, the medical information divided by service user and services corresponding thereto may be provided through an adjustment module, and a schedule according to the services may be adjusted.

The data may be divided by their types, and may be clustered, providing a connection function of platforms for managing resource.

Events generated by a touch operation and an interface function of accessing a cloud system in a smart phone may be processed, and data generated by the touch operation of a user and service software expressed as usable icons by user may be outputted and managed.

Also, events of a user received from a mobile device may be processed, and service information may be analyzed.

Software resources, hardware resources, and authority to use service application for checking the service state value from the user information and outputting service information may be managed, and authority transfer for service resources of a service resource scheduling module and service scheduling may be managed and distributed.

Data used by users may be divided by their types, and may be clustered to be stored in metadata database by data location, characteristics, and grade and retrieved by their characteristics.

Also, the cloud system for medical information processing may be managed, and a connection function of platforms for managing information resources may be provided.

A user receiving service application and medical information adjusted in accordance with the user grade may analyze medical information necessary for service in the mobile cloud system receiving a user operation of a smart phone as an event, and may secure its relationship to support decision-making necessary for medical service.

Also, the state value may be check according to the operation of the service event generated by a user in a smart phone terminal, and the access authority and the use of the service application for transmitting information necessary for service to a browser may be secured. All resources used for service may be managed by collecting software resources and hardware resources for service.

The service information provided to a user may be assigned with a storage space and service resources according to its utilization degree, which are monitored and managed. Limitations of resources and packet distribution for delivering information provided to a user may be outputted on a screen.

In order to provide medical information divided by user and services corresponding thereto through the medical information processing system, user grade adjustment and information access limitation for medical information processing may be managed, and service applications that are provided may be adjusted according to the grades of users who access the mobile cloud system supporting medial information integration processing.

The inventive concept relates to technology in which a user receives information processed in a smart phone terminal of a user in real-time according to user situations using a service building method and an information processing function of a mobile cloudy system, and can be utilized in the fields of information service development of cloud systems, smart business environment building, mobile medical information integration system, mobile health care service, home management service, and personalized service industries.

According to the embodiments of the inventive concept, medical information processing systems independently operated are integrated into one using a mobile cloud system. Since users using the integrated system are divided into grades, and a corresponding application provides a limited accessibility in a browser of a smart phone terminal, an optimized medical information service can be provided to a user.

Also, since real-time access is enabled without being limited to location and time of a user, diagnosis for an emergency patient and real-time medical treatment can be provided. In addition, it is possible to download a browser into a smart phone terminal and other network devices to which an embedded function is applied.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. A system for processing medical information through a medical terminal, comprising:
   a mobile cloud system unit;
   a service browser unit configured as an application in a user terminal to allow a user to use a medical information processing service, and inducing access to the mobile cloud system unit taking charge of medication information processing, and
   a medical information processing software module,
   wherein the service browser unit comprises:
   a user interface module providing a service application of an icon type to the user through access identification and location information of the user using a mobile browser;
   an event module generating event information for extracting a module for configuring a service necessary in each region of a mobile cloud server configuring the medical information processing service;
   a session module managing a network environment of the user and maintaining a connection situation according to a change of the network environment;
   a conversion module encoding and converting the location information of the user and the event information into a compression code according to a predetermined protocol;
   a security module encoding the location information of the user and the event information configured by the conversion module to securely configure virtualization of the mobile cloud server together with user access information;
   a network module delivering the location information of the user and the event information to the mobile cloud system unit and monitoring a network state; and
   a service handler configuring a user interface with information received from the mobile cloud system unit, sensing an interface touch operation, and monitoring a service operation, and
   the user configures user situation information showing a user situation in a smart phone to transmit to the mobile cloud system unit in real-time, and submits the user situation information generated in the user interface module and the event information generated in the event module to the mobile cloud system unit,
   wherein medical information processing software module comprise:
   an adjustment module providing medical information divided by service user and a service corresponding thereto;
   a scheduler module adjusting a schedule according to the service;
   a distributed data module dividing data by type and clustering the data; and
   a platform connection module providing a connection function of platforms managing resources, and usable in a smart phone and processing medical information in real-time,
   wherein the scheduler module comprises:
   a service resource scheduling module managing software resources, hardware resources, and authority to use service application for checking a service state value from the location information of the user and the event information and outputting service information; and
   a service distribution scheduling module managing and distributing medical information and service scheduling, and authority transfer for service resources of the service resource scheduling module, and
   wherein the service distribution scheduling module provides a function of assigning a storage space and service resources to the service information provided to the user according to utilization degree thereof and monitoring and managing the service information, and outputting details of resources and packet distribution for delivering the information provided to the user on a screen.

2. The system of claim 1, wherein the service browser unit comprises an interface function of accessing from a smart phone to a cloud system and a function of outputting and managing data generated by the user touch operation and service software processing an event generated by the touch operation and expressed as an icon usable by user.

3. The system of claim 1, wherein the scheduler module further comprises a medical information scheduling module processing an event of a user received from a mobile device and analyzing the service information.

4. The system of claim 1, wherein the distributed data module has a function of classifying data used by users, and clustering the data to store location, characteristics, and grade in a metadata database and retrieving the data by characteristics.

5. The system of claim 1, wherein the platform connection module provides a function of connecting between platforms for managing a cloud system for medical information processing and information resources and allows a smart phone terminal comprising a function of virtualizing resources necessary for service processing to access the cloud system.

6. The system of claim 3, wherein the medical information scheduling module provides a function of analyzing medical information necessary for service and securing a relationship therebetween to support a decision-making necessary for medical service, in a mobile cloud system receiving an operation that a user receiving medical information adjusted according to a user grade and service application performs in a smart phone as an event.

7. The system of claim 1, wherein the service resource scheduling module provides a function of checking the state value according to an operation of a service event generated from a smart phone terminal by a user, securing an authority to use and access a service application for transmitting information necessary for a service to a browser, and collecting software resources and hardware resources necessary for the service to manage all resources used for the service.

8. The system of claim 1, further comprising an adjustment module for providing medical information divided by service user and a service corresponding thereto, the adjustment module comprising:
- a user access adjustment module managing adjustment of user grades for processing and information access limitations and
- an application adjustment module adjusting and providing a service application provided according to the grade of a user connected to a mobile cloud system supporting medical information integration processing.

* * * * *